(12) United States Patent
Sheridan

(10) Patent No.: US 9,891,109 B2
(45) Date of Patent: Feb. 13, 2018

(54) PORTABLE COLOUR SENSOR

(71) Applicant: Nix Sensor Ltd., Hamilton (CA)

(72) Inventor: Matthew Sheridan, Burlington (CA)

( * ) Notice: Subject to any disclaimer, the term of this patent is extended or adjusted under 35 U.S.C. 154(b) by 130 days.

(21) Appl. No.: 14/974,040

(22) Filed: Dec. 18, 2015

(65) Prior Publication Data

US 2016/0238450 A1    Aug. 18, 2016

Related U.S. Application Data

(60) Provisional application No. 62/116,966, filed on Feb. 17, 2015.

(51) Int. Cl.
| | | |
|---|---|---|
| *G01J 3/46* | (2006.01) | |
| *G01J 3/50* | (2006.01) | |
| *G01N 21/25* | (2006.01) | |
| G01N 21/47 | (2006.01) | |

(52) U.S. Cl.
CPC .............. *G01J 3/50* (2013.01); *G01N 21/251* (2013.01); *G01N 2021/4757* (2013.01); *G01N 2201/0221* (2013.01); *G01N 2201/062* (2013.01); *G01N 2201/08* (2013.01)

(58) Field of Classification Search
CPC . G01J 3/50; G01N 21/251; G01N 2021/4757; G01N 2201/0221; G01N 2201/062; G01N 2201/08

USPC ......................................................... 356/402
See application file for complete search history.

(56) References Cited

U.S. PATENT DOCUMENTS

| | | | | |
|---|---|---|---|---|
| 5,963,333 A * | 10/1999 | Walowit | ................ | G01J 3/0251 356/328 |
| 8,705,018 B2 * | 4/2014 | Benderly | ................ | G01N 21/87 356/30 |
| 2005/0041926 A1 * | 2/2005 | Elkins, II | ............. | G02B 6/3887 385/53 |

* cited by examiner

*Primary Examiner* — Hina F Ayub
(74) *Attorney, Agent, or Firm* — Ridout & Maybee LLP; Mark A. Koch

(57) ABSTRACT

The present concept is a portable color sensor for measuring color of a substrate that includes a single flat printed circuit board with a top and bottom side which includes at least one LED light and one color sensor and at least one light pipe receiving light from the LED and transmitting it onto a substrate at an angle theta. It also includes a tube frame including an optical tube for receiving light reflections from the substrate and directing the reflections to the color sensor. The light pipes and the tube frame, are mounted and compression fit between the printed circuit board and a lower housing.

13 Claims, 4 Drawing Sheets

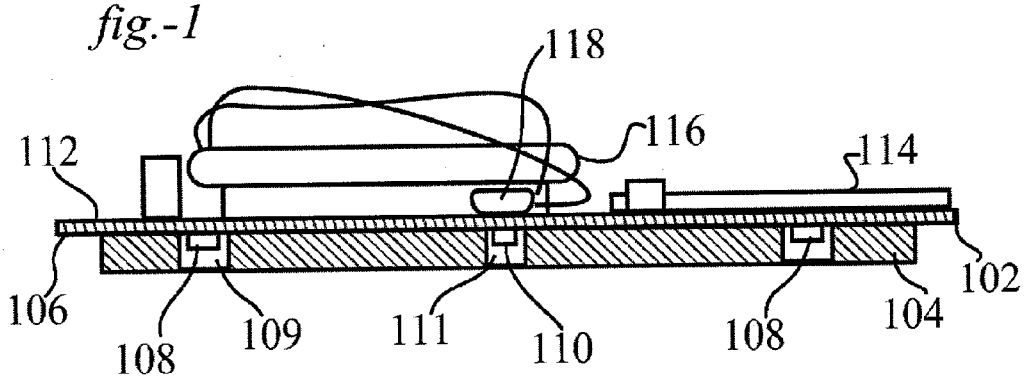
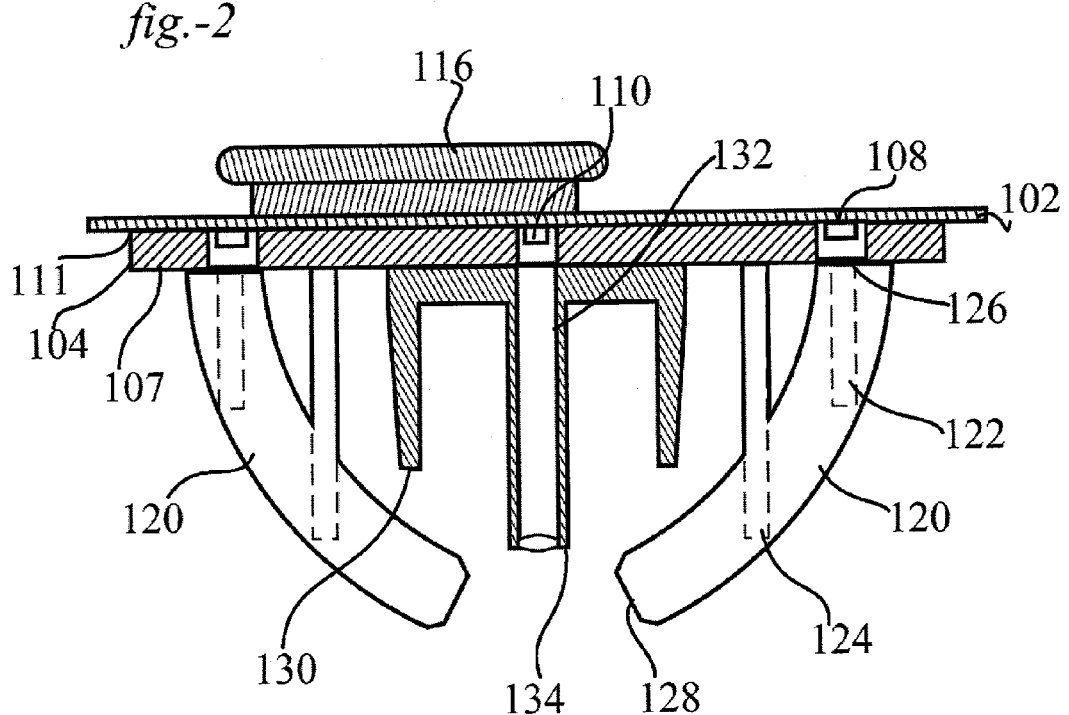

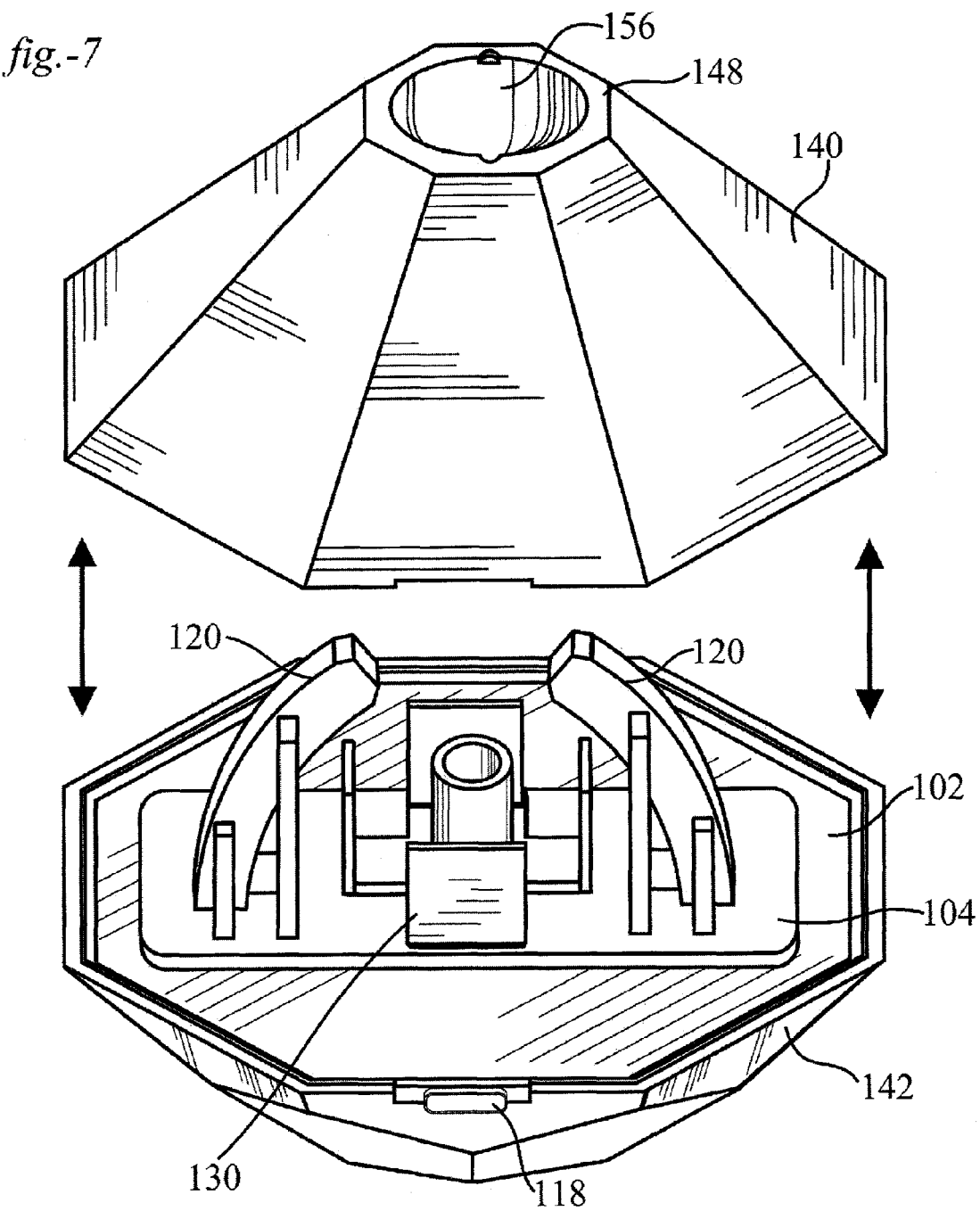

PORTABLE COLOUR SENSOR

This application claims priority from the previously filed provisional application No. 62/116,966, filed on Feb. 17, 2015 by Nix Sensor Ltd. under the title: PORTABLE COLOUR SENSOR.

FIELD OF THE INVENTION

The present concept relates to a device for measuring and analysing colours and more particularly it relates to small handheld inexpensive colour measuring device which can interface via Bluetooth with smartphones and convert the colour readings into any number of current colour models, or spaces.

BACKGROUND OF THE INVENTION

There is a need to quickly and accurately be able to measure colours on a variety of different surfaces and convert the colour measurement into a number of standard colour spaces.

There are a number of prior art devices which have attempted to measure colour each with shortcomings normally related to accuracy reproducibility, portability, cost of manufacture and inability to convert readings into a number of standard colour spaces used by different industries.

SUMMARY OF THE CONCEPT

The present concept a portable colour sensor for measuring colour of a substrate includes:
a) a single flat printed circuit board with a top & bottom side which includes at least one LED light and one colour sensor;
b) at least one light pipe receiving light from the LED and transmitting it onto a substrate at an angle theta;
c) a tube frame including an optical tube for receiving light reflections from the substrate;
d) wherein the light pipes and the tube frame, are compression fit between the printed circuit board and a lower housing.
e) wherein the lower housing includes at least one light pipe rib for each light pipe and the light pipes include at least one flange co-operating with at least one slot defined in the light pipe rib for slideably receiving the flange in the slot, for holding the light pipe in place.

Preferably wherein the LED light directed perpendicularly away from the printed circuit board and wherein the light pipe is an arcuate member bending the light to achieve the angle theta.

Preferably wherein the light pipe abutting at one end to the LED and connecting at the other end at a light emitting port in the lower housing.

Preferably wherein the light emitting port is located within a light cavity.

Preferably wherein the light cavity is an inverted dome with the bottom terminating at a contact surface.

Preferably wherein the optical tube terminating at one end at a receiving port in the dome and at the other end terminates proximate the colour sensor.

Preferably wherein the receiving port located at the crown of the dome. Preferably the contact surface is an annular ring abutting against the substrate thereby minimizing external light from entering into the light cavity. The printed circuit board includes a planar gasket mounted to the bottom side, the gasket includes openings for the LED light to pass through and for the light reflection to pass through to the color sensor. Preferably the gasket includes a sealing surface onto which the tube frame and at least one light pipe are butted against. The lower housing includes a cylindrical tube receiver for slideably receiving the tube end of the optical tube therein. Preferably there is an upper housing for abutting against the topside of the printed circuit board and the lower housing, thereby encapsulating the printed circuit board within the upper and lower housing. Preferably the angle theta is 45°.

BRIEF DESCRIPTION OF THE DRAWINGS

The present concept will be described by way of example only with reference to the following drawings in which:

FIG. 1 is a partial side cross sectional view of the printed circuit board used in the present concept together with the gasket mounted on the bottom side and electrical components on the top side.

FIG. 2 is a schematic partial cross sectional view of the printed circuit board shown together with an optical tube and light pipes mounted onto a sealing surface of a gasket.

FIG. 7 is an inverted schematic exploded view of the printed circuit board together with the tube frame, light pipes, and the lower and upper housings.

DETAILED DESCRIPTION OF THE PREFERRED EMBODIMENTS

Figure 3:
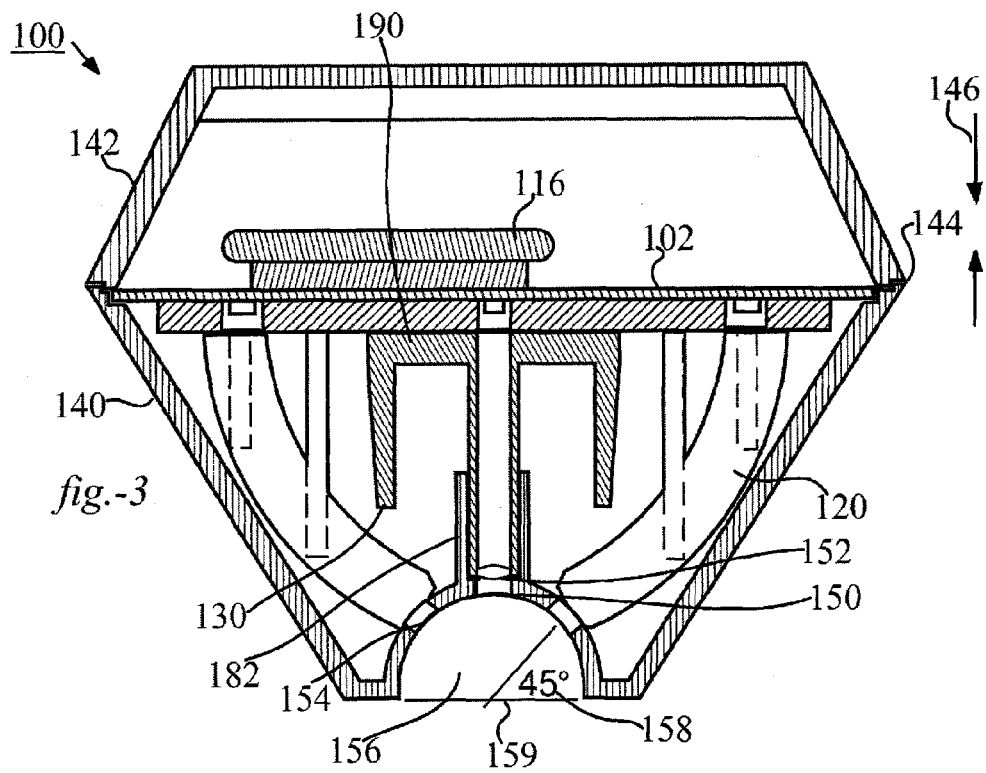
FIG. 3 is a schematic cross sectional view of the print circuit board together with light pipes and a tube frame mounted in a lower housing and an upper housing.

Components of the present concept the portable colour sensor 100 are depicted in the attached figures and shown in various stages of assembly and completion for the benefit of the reader.

FIG. 1 for example shows the single printed circuit board PCB 102 used in the present concept together with a planar gasket 104 mounted on a bottom side 106 having openings 109 for LEDS 108 and opening 111 for colour sensor 110. Colour sensor 110 is a true colour sensor rather than an RGB sensor.

PCB 102 includes a top side 112 at least one integrated circuit 114 a battery 116 and a hard wired interface namely a micro USB port 118 for calibration and data exchange purposes.

FIG. 2 shows the orientation of various additional components relative to the print circuit board 102 namely left and right light pipes 120 each also having a first flange 122 and a second flange 124, a receiving end 126 and a transmitting end 128. Receiving end 126 abuts against gasket 104 in order that light from LEDS 108 can be transmitted down through light pipe 120 and out through transmitting end 128.

Further there is a tube frame 130 which includes an optical tube 132 having a tube end 134 also abutting and mounted onto gasket 104 for receiving light through optical tube 132 and transmitting the received light onto colour sensor 110.

The components are not assembled in the condition shown in FIG. 2 but rather only the orientation of these components relative to the print circuit board in shown in FIG. 2.

FIG. 3 shows the assembly of the printed circuit board 102 together with the light pipes 120 and the tube frame 130 all mounted into lower housing 140 and capped off with an upper housing 142 at a joint 144. All of the internal components are compression fit show by arrows 146 wherein the PCB 102 is urged downwardly into lower housing 140 thereby pushing downwardly upon the light pipes 120 and tube frame 130, in effect creating a sandwich effect wherein the light pipes 120, tube frame 130 and dust cover 152 are held in place.

Lower housing 140 also includes a lens dust cover 152, a receiving port 150 and defines a contact surface 148. Lower housing 140 also includes light emitting ports 154 and a light cavity 156. Light enters through light emitting ports 154 at an angle theta 158.

Figure 4:
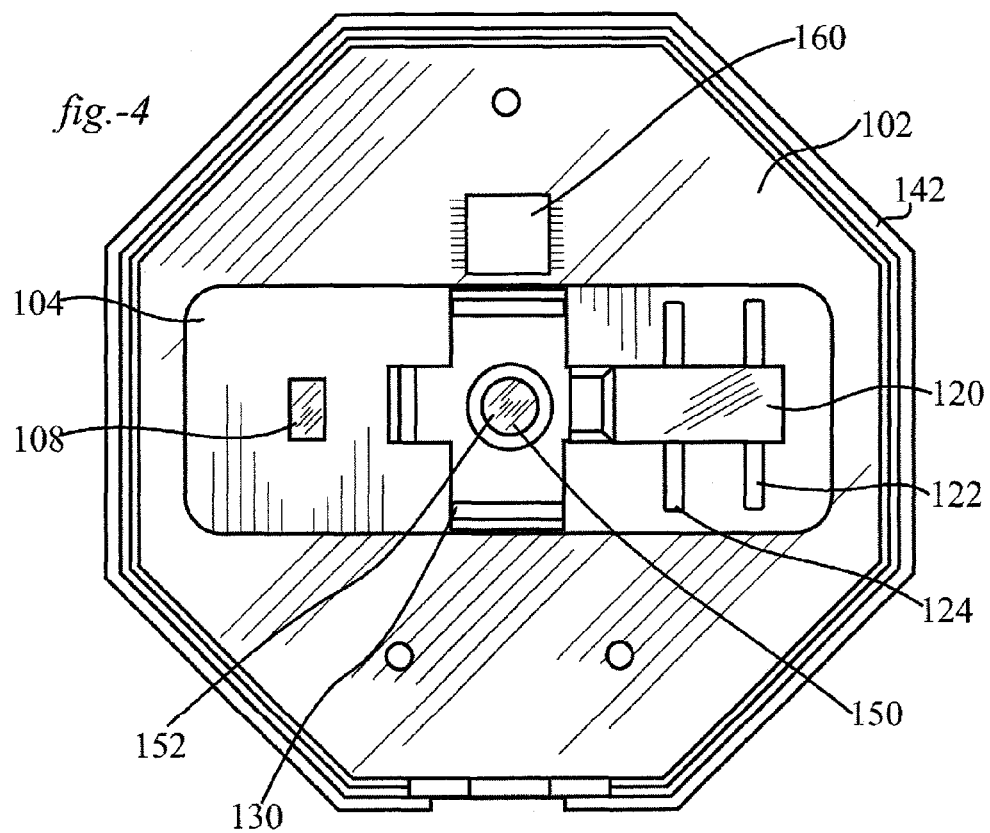
FIG. 4 is a top schematic plan view of the print circuit board mounted into the lower housing.

FIG. 4 is a schematic plan view of the bottom side 106 of printed circuit board 102 with one light pipe 120 shown in position wherein on the other side the LED 108 is clearly visible through opening 109 in gasket 104. Also shown in position is tube frame 130 and dust cover lens 152 at the bottom of receiving port 150. Additionally the first and second flanges 122 and 124 of light pipe 120 are also visible together with the joint 144 of the upper housing 142.

Figure 5:
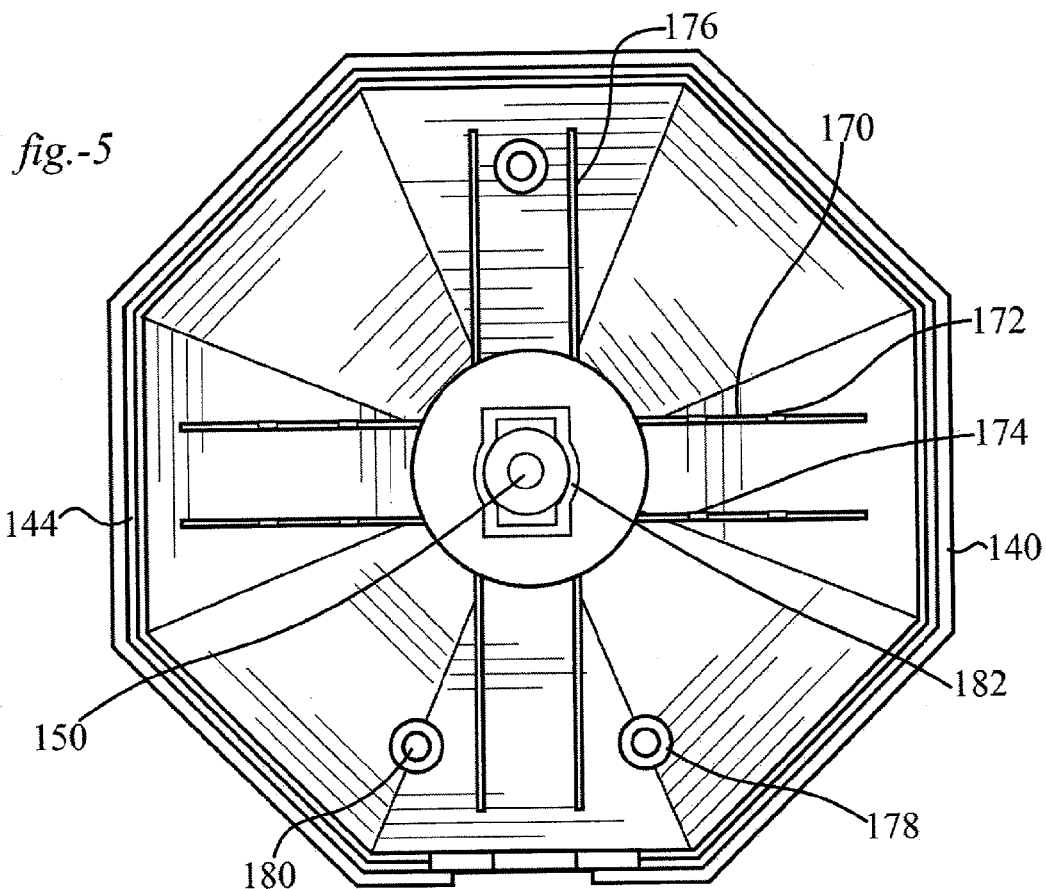
FIG. 5 is a top plan view of the lower housing prior to the installation of the light pipes and tube frame and printed circuit board.
Figure 6:
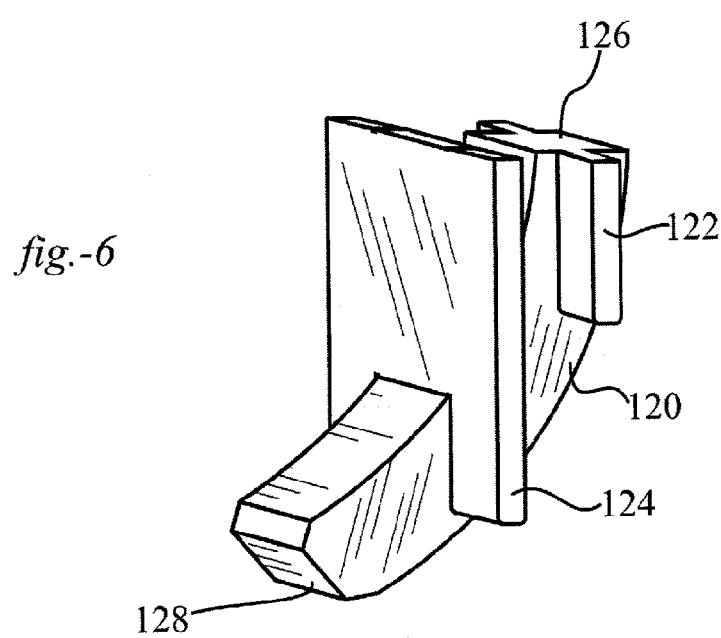
FIG. 6 is schematic perspective view of the light pipe.

FIG. 5 is a plan view looking into the cavity of lower housing 140 with all of the components removed showing a set of four light pipe ribs 170 each having a first slot 172 and a second slot 174 that register and slideably engage with first flange 122 and second flange 124 respectively of light pipe 120.

There are four additional support ribs 176 upon which the printed circuit board 102 rests and three abutments 178 each with a screw hole 180 for fastening print circuit board onto lower housing 140.

The reader will see that the first flange 122 slideably engages with first slot 172 and second flange 124 of light pipe 120 slideably engages with second slot 174. In this manner light pipes 120 are slideably urged into position into the lower housing 140. Additionally dust cover lens 152 is placed into the bottom of tube receiver 182 and optical tube 132 is slideably received within tube receiver 182 thereby placing tube frame 130 in place into lower housing 140.

Thereafter PCB 108 is adhered to with gasket 104 at contact surface 111 is further placed with sealing surface 107 on top of the light pipes and the tube frame 130 thereby compressing gasket 104 which is made of a resiliently biased material in order to create a seal around the base 190 of tube frame 130 and also a seal around the receiving end 126 of light pipe 120 thereby ensuring that light which is conducted down light pipe 120 is not inadvertently transmitted into optical tube 132 directly from LED 108 or indirectly from light pipes 120. Contact surface 111 and sealing surface 107 preferably have pressure sensitive adhesive thereon.

FIG. 7 schematically shows the orientation of lower housing 140 relative to the upper housing 142 and the print circuit board 102 and the light pipes 120 and the tube frame 130.

FIG. 3 shows the angular relationship theta 158 of the light relative to the contact surface 148. This geometrical layout is often referred to as a 45/0 geometry in which illumination of the sample is accomplished at an angle of 45° and the colour sensor 110 receives a portion of the light reflected from the sample at an angle of approximately 0° plus or minus 8°. This geometry is used in order to minimize specular reflections and allow only few reflections to be transmitted through the optical tube 132.

In order to reduce manufacturing costs, time and componentry light pipes 120 have been configured such that a single flat print circuit board PCB 102 can be utilized to mount all of the electrical and electronic componentry.

The LEDS used have a broad parallel spectrum of visible light such that all wavelengths of visible light are emitted by the LEDS 108. In order to ensure consistency and reproducibility components having extremely low drift and low temperature coefficient variances are utilized throughout the device.

Readings obtained from the colour sensor are fed through on board integrated circuitry processing units which provide a predictable, stable and reproducible output.

The unit includes an integral Bluetooth transmission device for wirelessly transmitting data to a smartphone which together with a smartphone application for presenting the data in usable format.

It is also possible to communicate through a hardwired mini USB port 118 to a laptop or other computer. The device is calibrated through the hardwired mini USB port 118 prior to the shipping.

The outputs are converted into usable colour spaces including the well known RGB colour space, HSL colour space, HSV colour space, LAB colour space, XYZ colour space and is also converted into HTML, CMYK or Pantone® units. The processor software application is able to convert to any print system using a delta e calculation to determine what available paint is closest (mathematically) to the scanned sample.

The contact surface 148 is an annular ring placed against a substrate or surface 159 to be analysed for colour such as a painted wall, skin, and a host of other surfaces and materials.

Light emitted from is conducted down light pipes 120 and exits into light cavity 15 at an angle theta 158 onto a substrate 159 to be measured. Some of the light is reflected back up optical tube 132 where it is received by color sensor 110 and a measurement is taken and recorded.

It should be apparent to persons skilled in the arts that various modifications and adaptation of this structure described above are possible without departure from the spirit of the invention the scope of which defined in the appended claim.

I claim:

1. A portable colour sensor for measuring colour of a substrate, the sensor comprising:
    a) a single printed circuit board with a top & bottom side which includes at least one LED light and one colour sensor; mounted onto the bottom side;
    b) at least one light pipe receiving light from the LED and transmitting it onto a substrate at an angle theta;
    c) a tube frame including an optical tube extending perpendicular from the printed circuit board, for receiving light reflections from the substrate and directing the reflections to the colour sensor;
    d) wherein the light pipes and the tube frame, are mounted and compression fit between the printed circuit board and a lower housing;
    e) wherein the lower housing includes at least one light pipe rib for each light pipe and the light pipes include at least one flange co-operating with at least one slot defined in the light pipe rib for slideably receiving the flange in the slot, for holding the light pipe in place.

2. The portable colour sensor claimed in claim 1 wherein the LED light is directed perpendicularly away from the printed circuit board and wherein the light pipe is an arcuate member conducting the light within the alternate member to achieve the angle theta, relative to the substrate.

3. The portable colour sensor claimed in claim 2 wherein the angle theta is preferably 45°.

4. The portable colour sensor claimed in claim 1 wherein the light pipe abuts at one end to the LED and connects at the other end to a light emitting port in the lower housing.

5. The portable colour sensor claimed in claim 4 wherein the lower housing includes a light cavity and wherein the light emitting port is located within a light cavity.

6. The portable colour sensor claimed in claim 5 wherein the light cavity is an inverted dome cavity with the bottom terminating at a contact surface.

7. The portable colour sensor claimed in claim 6 wherein the optical tube terminates at one end at a receiving port in the dome and at the other end terminates proximate the colour sensor.

8. The portable colour sensor claimed in claim 7 wherein the receiving port is located at the crown of the dome.

9. The portable colour sensor claimed in claim 6 wherein the contact surface is an annular ring abutting against the substrate thereby minimizing external light from entering into the light cavity.

10. The portable colour sensor claimed in claim 1 wherein the printed circuit board includes a planar gasket mounted to the bottom side, the gasket includes openings for the LED light to pass through and for the light reflection to pass through to the color sensor.

11. The portable colour sensor claimed in claim 10 wherein the gasket includes a sealing surface onto which the tube frame and at least one light pipe are butted against.

12. The portable colour sensor claimed in claim 1 wherein the lower housing includes a cylindrical tube receiver for slideably receiving the tube end of the optical tube therein.

13. The portable colour sensor claimed in claim 1 further includes an upper housing for abutting against the topside of the printed circuit board and the lower housing, thereby encapsulating the printed circuit board within the upper and lower housing.

* * * * *